United States Patent [19]

Eaton

[11] Patent Number: 4,918,914
[45] Date of Patent: Apr. 24, 1990

[54] YARN QUALITY MONITORING METHOD AND APPARATUS

[75] Inventor: David C. Eaton, Buxton, United Kingdom

[73] Assignee: Rieter Scragg Limited, Cheshire, England

[21] Appl. No.: 123,242

[22] Filed: Nov. 20, 1987

[30] Foreign Application Priority Data

Dec. 11, 1986 [GB] United Kingdom ............... 8629597

[51] Int. Cl.⁵ ............... D02G 1/02; D01H 13/26; D01H 13/32; G06F 15/46
[52] U.S. Cl. ............... 57/264; 28/248; 57/265; 57/284; 57/290; 57/291; 73/160; 226/42
[58] Field of Search .............. 28/248; 226/42; 73/160; 57/264, 265, 290, 291, 284

[56] References Cited

U.S. PATENT DOCUMENTS

| | | |
|---|---|---|
| 3,333,467 | 8/1967 | Hoskins ............... 73/160 |
| 3,726,137 | 4/1973 | Denton ............... 28/248 X |
| 3,762,220 | 10/1973 | Gusack et al. ............... 73/160 |
| 4,012,816 | 3/1977 | Hatcher ............... 28/248 |
| 4,295,252 | 10/1981 | Robinson et al. ............... 28/248 |
| 4,309,801 | 1/1982 | Feffer ............... 28/248 |
| 4,581,884 | 4/1986 | Brough ............... 57/291 |
| 4,839,815 | 6/1989 | Eaton et al. ............... 57/265 X |

FOREIGN PATENT DOCUMENTS

| | | |
|---|---|---|
| 841255 | 7/1960 | United Kingdom . |
| 1051886 | 12/1966 | United Kingdom . |
| 1065671 | 4/1967 | United Kingdom . |
| 1184586 | 3/1970 | United Kingdom . |
| 1219666 | 1/1971 | United Kingdom . |
| 1249610 | 10/1971 | United Kingdom . |
| 1492662 | 11/1977 | United Kingdom . |
| 1545609 | 5/1979 | United Kingdom . |
| 1552474 | 9/1979 | United Kingdom . |
| 8302665 | 8/1983 | World Int. Prop. O. . |

Primary Examiner—John Petrakes
Attorney, Agent, or Firm—Oblon, Spivak, McClelland, Maier & Neustadt

[57] ABSTRACT

A method of monitoring yarn quality in a yarn texturing process comprises measuring the velocity of the travelling yarn at two locations and comparing the measured velocities. At a first location the yarn tension is sufficient to draw out the crimp and at a second location the tension is lower such that the crimp is developed. Apparatus for performing this method comprises a measuring device to measure the peripheral speed of a driving roller which is part of a nip-feed device serving to feed a crimped yarn at the first location from a false twist device to a second heater of a false twist texturing machine. At the second location between the second heater and a third feed device of the machine is a second velocity measuring device which comprises an inlet tube, an outlet tube and two discs of brass which form spaced measuring stations spaced by an insulating body. Signals proportional to the static electrical charge carried by the yarn as is passes through the measuring device are sent from the discs to an amplifier and calculating means, at which the speed of travel of the yarn between the discs is calculated.

20 Claims, 6 Drawing Sheets

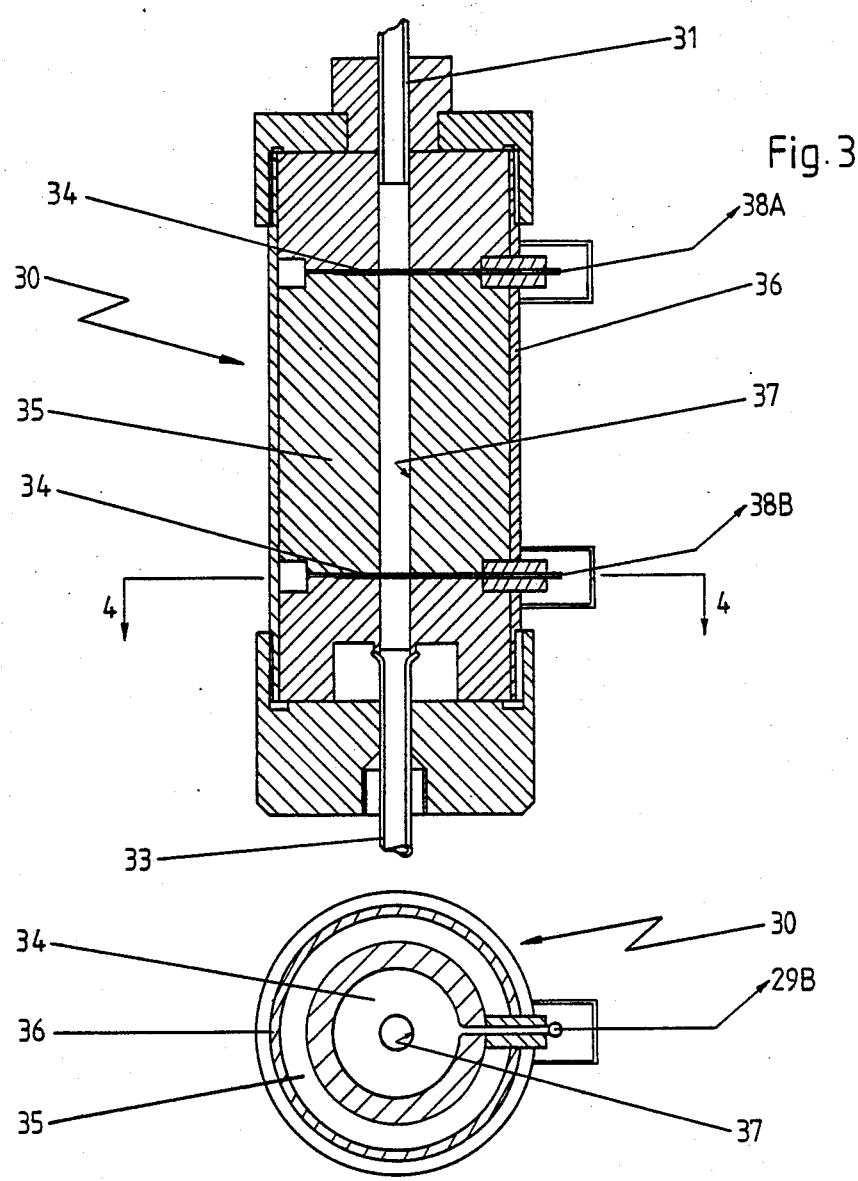

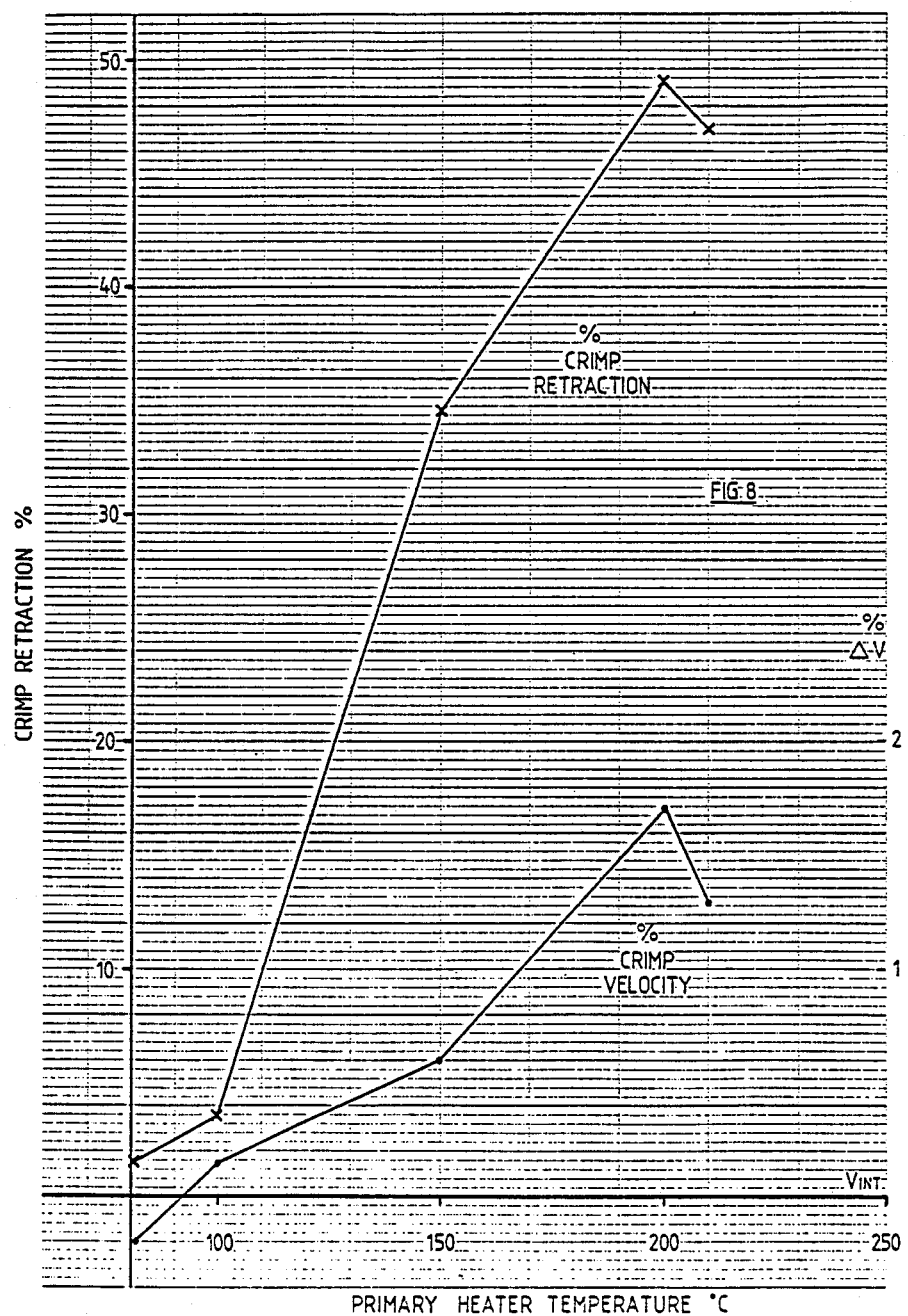

YARN QUALITY MONITORING METHOD AND APPARATUS

This invention relates to a yarn quality monitoring method, and apparatus for use in such method, and in particular to a method of and apparatus for on-line monitoring of the "crimp velocity" of textured yarn, which can be related to off-line "bulk level" or "crimp retraction" measurements.

Bulk level or crimp retraction is a measure of the amount of crimp which has been put into the yarn by the texturing process. It can be measured conventionally by a test in which a hank of yarn, after preheating in air, is measured for length under a high load sufficient to pull out the crimp and again under a low load sufficient only to stabilise the fibres but retain the maximum crimp. The bulk level is then defined as the difference between the measured lengths expressed as a percentage of the first length.

The above test is carried out on a crimped yarn, and if it is desired to measure the effect of varying the parameters controlling the crimping process, it is necessary to run a separate test for each parameter variation and measure the bulk level of each sample thus produced. In addition, although in test conditions yarn samples may be taken from the beginning, end and any number of intermediate stages of the run, this is not practicable when crimping yarn commercially, since the test is destructive of the samples taken. In consequence, it is not possible to check by the above method of consistency of the bulk level produced in a commercial crimping operation.

It is an object of the present invention to provide a method of, and apparatus for, determining the quality of a textured yarn, in a manner which can be related to the off-line bulk test, continuously throughout is commercial texturing operation.

The invention provides a method of monitoring yarn quality in a yarn texturing process, comprising the steps of measuring a first velocity of yarn whilst forwarding the textured yarn under a first tension sufficient to draw out the crimp, measuring a second velocity of the yarn whilst forwarding the textured yarn under a second tension insufficient to draw out the crimp and determining a crimp velocity value from said yarn velocity measurements.

The method may comprise false-twist crimping the yarn prior to performing said velocity measuring steps, and may comprise drawing said yarn simultaneously with said false twist crimping thereof.

Said first velocity measurement may be effected by measuring the peripheral speed of yarn feed device, which feed device is operable to feed the yarn from a crimping region to a subsequent processing region. In said subsequent processing region the yarn may be wound onto a package or may be heated under said second tension prior to being wound onto a package.

Said second velocity measurment may be effected by detecting, at two spaced locations in said subsequent processing region, a parameter of said yarn which moves with the yarn, and measuring the elapsed time between such detections. Preferably the second velocity measuring step comprises detecting at said two locations a static charge carried by the yarn.

The invention also provides apparatus for performing the above mentioned method comprising first forwarding and tensioning means operable to forward a textured yarn under a first tension sufficient to draw out the crimp therein, first velocity measuring means operable to measure the velocity of the textured yarn whilst it is forwarded under said first tension, second forwarding and tensioning means operable to forward said textured yarn under a second tension insufficient to draw out the crimp, and second velocity measuring means operable to measure the velocity of the textured yarn whilst it is forwarded under said second tension. The apparatus may also comprise calculating means operable to determine the yarn quality from said velocity measurements.

The apparatus may comprise false twist crimping apparatus, and said first forwarding and tensioning means may be operable to draw said yarn simultaneously with the false twist crimping thereof.

Said first forwarding and tensioning means may comprise a feed device, which may be operable to feed the yarn from a crimping apparatus to a subsequent processing apparatus. Said first velocity measuring means may be operable to measure the peripheral speed of said feed device may comprise a driving roller and a roller forming a nip therewith through which said yarn may pass. Said subsequent processing apparatus may comprise package winding means, and may also comprise yarn heating means disposed upstream thereof.

Said second velocity measuring means may comprise detecting means operable to detect at two spaced locations a parameter of the yarn which moves with the yarn, and time measuring means operable to measure the elapsed time between such detectors. Preferably the detecting means comprises static electrical charge measuring means.

The invention also provides apparatus for measuring the velocity of a travelling yarn comprising a housing defining a path of travel of the yarn therethrough, a pair of measuring stations spaced along said yarn path within said housing, and at each measuring station, a sensor adapted to detect the presence of a static electrical charge on said yarn and to produce an electrical signal proportional to the value of such static electrical charge. Each sensor may comprise a disc of an electrically condutctive material having an aperture therein through which a yarn may pass. Said disc may be separated by body of an electrically insulating material;and said housing may comprise a case of an electrically conductive material and which encloses said discs and said insulating body.

One embodiment of apparatus in accordance with the invention will now be described with reference to the accompanying drawings in which FIG. 1 is a schematic end elevation of a false twist crimping machine embodying the apparatus of the invention.

FIG. 3 is a longitudinal section of the second velocity measuring means of FIG. 2.

FIG. 4 is a sectional plan view on the line 4—4 of the second velocity measuring means of FIG. 3.

FIG. 8 shows a relationship between crimp velocity and bulk level.

Figure 1:
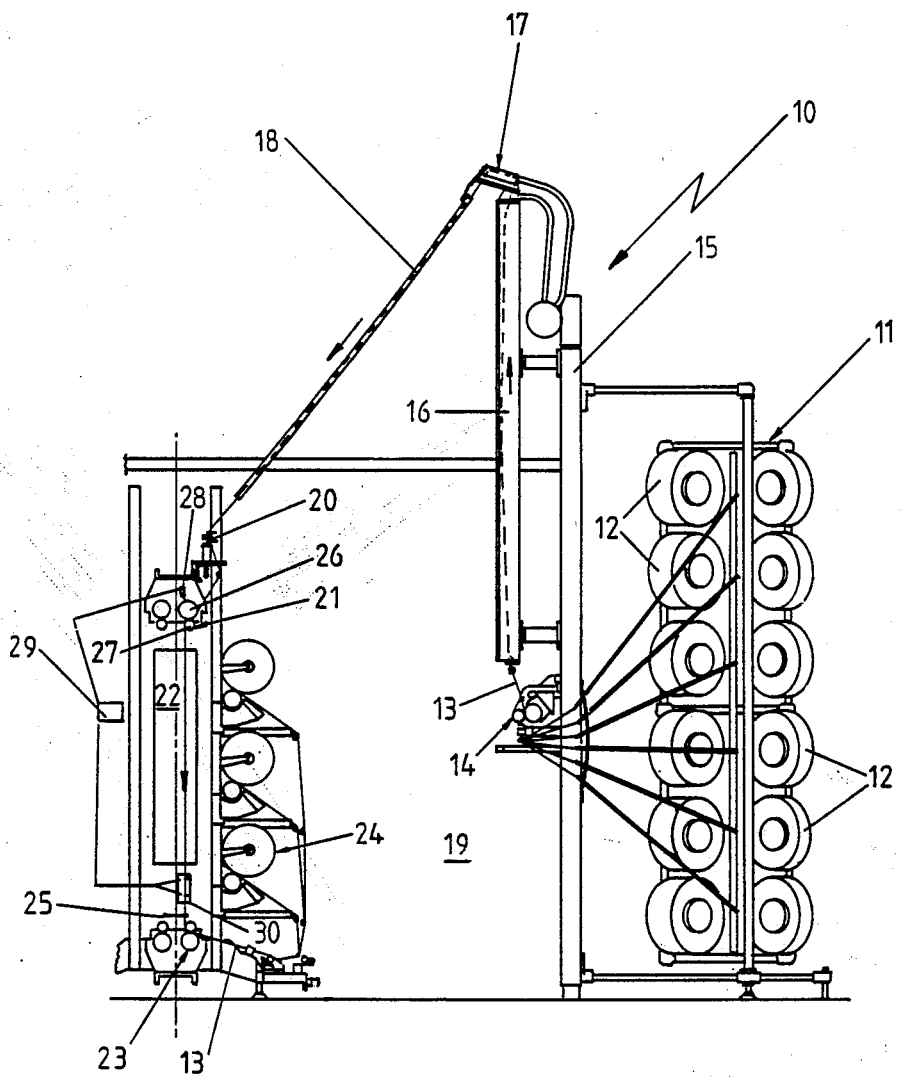

Referring now to FIG. 1 there is shown a false twist crimping machine 10 comprising a creel 11 having several packages 12 thereon of uncrimped, undrawn or partially drawn, yarn. A yarn 13 is withdrawn from a package 12 by a first feed roller device 14 mounted on a support 15 of the creel 11. The yarn 13 is then passed over an upstanding primary heater 16 which is also mounted on the support 15. A guide arrangement 17 at the top of the heater 16 guides the yarn 13 to a cooling plate 18, which extends downwardly over the operator's aisle 19 to guide the yarn 13 to a false twist device 20. The false twist device 20 serves to insert twist into the yarn 13 extending thereto from the first feed roller device 14, and a second or intermediate feed roller device 21 serves to draw such length of yarn 13 simultaneously with the twist insertion. The now crimped yarn 13 then passes through a subsequent processing region in which is provided a secondary heater 22, a third feed roller device 23 and a package winding apparatus 24. Apparatus as thus described is conventional for the production of set yarns. If however stretch yarns are required the aforementioned secondary heater 22 is omitted and the yarn 13 passes directly from the second feed roller device 21 to the package winding apparatus 24. In either case one or more yarn guides 25 may be provided before the winding apparatus 24.

The yarn 13, as it arrives at the second feed roller device 21, is crimped but is under such a relatively high tension that the crimp is pulled out. Between the second feed roller device 21 and the yarn guide 25 the yarn 13 is crimped and is under a relatively low tension sufficient only to stabilise the fibres but such as to allow full crimp to be developed. If the yarn velocities in these two regions are measured as being V1 and V2 respectively, then the quantity $(V1-V2)/V1 \times 100$ may be defined as the "crimp velocity" and can be shown to have a positive relationship to the bulk level or crimp retraction defined as $(L1-L2)/L1 \times 100$ where L1 and L2 are the lengths of the yarn under the same tension conditions when measured in an off-line test as previously described.

The velocity V1 of the crimped yarn 13 as it arrives at the second feed device 21 is equal to the peripheral speed of that feed device. The feed device 21 comprises a driving roller 26 and a driven roller 27 forming with each other a nip through which the yarn 13 passes. A first velocity measuring device 28 of any conventional type is provided to measure the peripheral speed of the driving roller 26 and hence V1. A signal proportional to the speed V1 is sent by the measuring device 28 to a calculating means 29.

A second velocity measuring device 30 is provided n the subsequent processing region between the second feed device 21 and the yarn guide 25. The measuring device 30 provides a signal which contains information from which the yarn velocity V2 in this region can be calculated, the signal being amplified by amplifier 38 and then also being transmitted to the calculating means 29. The calculating means 29 is operable to calculate the quantity $(V1-V2)/V1 \times 100$ which is the crimp velocity.

By this means the yarn quality can be continuously monitored throughout the texturing operation. In addition transient variations, which cannot be detected by the off-line static sampling method, may be detected by the method of the present invention.

Figure 2:
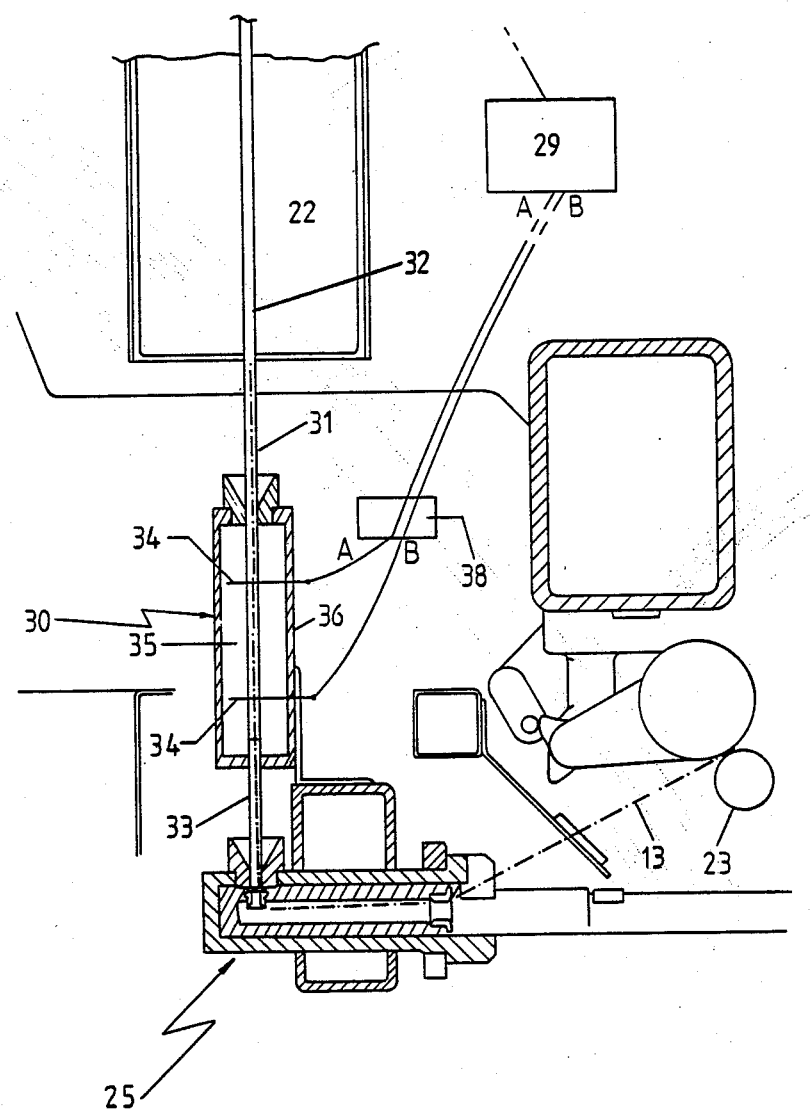
FIG. 2 is a sectional elevation of part of a machine similar to that of FIG. 1, showing the second velocity measuring means.

Conveniently the second velocity measuring device 30 may be located between the seconday heater 22, if one is present, and the yarn guide 25 as shown in FIG. 1. A similar arrangement is shown in FIG. 2 in greater detail but with a slightly different machine layout. In this case the yarn guide 25 serves to turn the yarn 13 through 90° to direct it to the third feed roller device 23 in the manner and for the purpose described in GB patent No. 2147323. The second velocity measuring device 30 has an inlet tube 31, which may be attached to or be part of the inner tube 32 of secondary heater 22, and an outlet tube 33 which serves as an entry tube for the yarn guide 25. By this means threading of the yarn 13 through the device 30 may be effected simultaneously with the threading of the yarn 13 through the heater 22 and yarn guide 25 using a suction gun as is described in GB patent No. 2147323 corresponding to U.S. Patent No. 4,581,884.

The velocity measuring device 30 provides two measuring stations a fixed distance apart, for example 200 mm. At each measuring station is located a disc 34 of a suitable electrically conducting material, such as brass, and each 34 is connected to a respective input A or B of the amplfiier 38 and then to the calculating means 29. The discs 34 are separated by a body of an insulating material 35, eg ceramic, air, plastics material, the latter being a high temperature plastics material if the heater 22 is positioned adjacent the device 30, and are enclosed in an earthed, electrically conductive case 36 so as to form a screen against extraneous pick-up of static electricity. As is more clearly seen in FIGS. 3 and 4 the discs 34 and insulation body 35 are provided with a central hole 37 through which the yarn 13 passes without contact from the inlet tube 31 to the outlet tube 33. As the yarn 13 passes each disc 34 a signal is transmitted from that disc 34 via amplifier 38 to the calculating means 29 proportional at any given instant to the quantity of static electrical charge carried by that part of the yarn 13 passing through the hole 37 of that disc 34 at that instant.

The velocity measurement is based on the fact that the distribution of the static electrical charge value along the yarn 13 is random, and that the time taken for a charge value pattern detected at the first measuring station to be repeated at the second measuring station will enable the velocity of the yarn to be determined. The time taken is determined by applying a delay to the signal from the first measuring station and correlating the delayed signal with the signal from the second measuring station. The correlation will be a maximum when the two signals coincide, ie when the delay applied to the first signal is equal to the time taken for a given part of yarn 13 to travel between the two discs 34.

Figure 5:
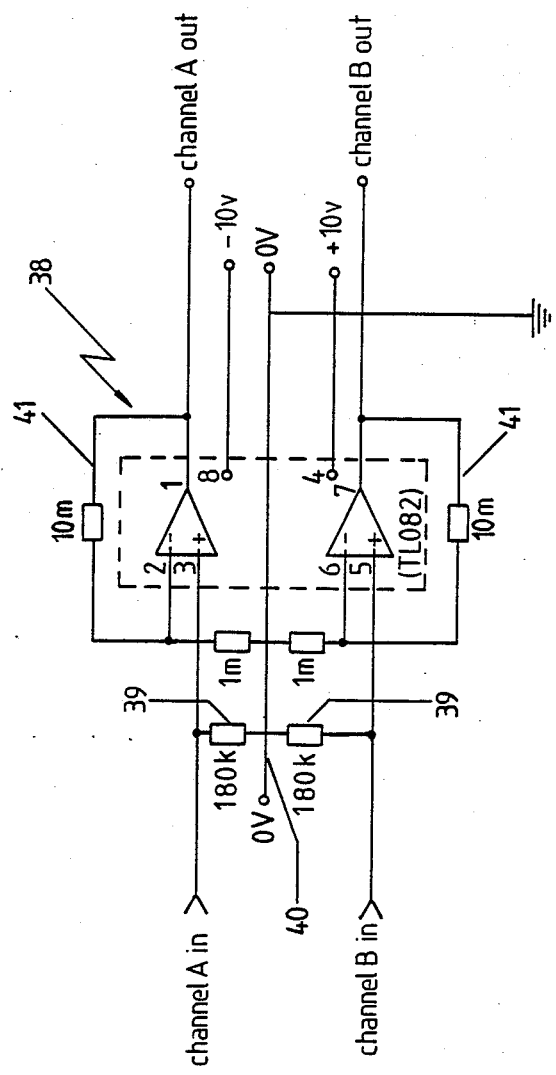
FIG. 5 shows as arrangement of an amplifier of the velocity measuring means.

The signals from the two discs 34 are fed to the inputs A-in and B-in of an amplifier 38 of the velocity measuring means 30, the amplifier 38 being shown in FIG. 5. The amplifier 38 is a modified form of a standard high impedance, non-inverting, negative feedback operational amplifier. The modification comprises the provision of a leakage resistor 39 between each inputs A-in, B-in and the zero volt (earth) lead 40. The resistors 39 have a compromise value, for example 180 K$\Omega$, which is low enough to give sufficient leakage to earth to provide an adequate signal from the feedback loop 41, but is high enough to prevent too much drainage of the signal at input A-in from the first measuring station and hence insufficient charge remaining to be carried to the second measuring station. The output signal from the amplifier 38 represents the voltage differences at the points 2−, 3+ and 5+, 6−, such voltage differences being amplified by a factor of 10. Correlation of the output signals A-out, B-out is performed in the calculating means 29 in conventional manner, leading to a calculation of the velocity V2 of the yarn 13 in its crimp developed condition in the subsequent processing region between the second feed device 21 and the yarn guide 25. The velocity V1 of the yarn 13 in its crimp pulled out condition is determined by the measuring device 28 as previously described, and the value of the crimp velocity, as determined by the relationship (V1−V2)/V1×100, is calculated by the calculating means 29, noting that the crimp velocity has a direction opposite to the direction of yarn travel.

Figure 6:
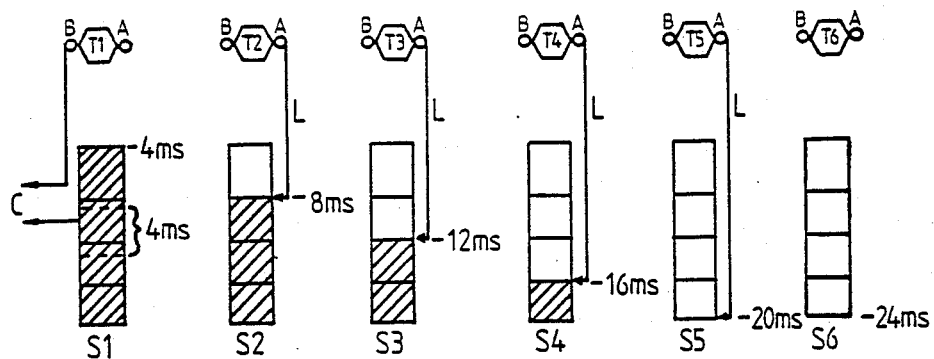
FIG. 6 and 7 show the arrangement of a signal store of the calculating means associated with consecutive machine positions.
Figure 7:
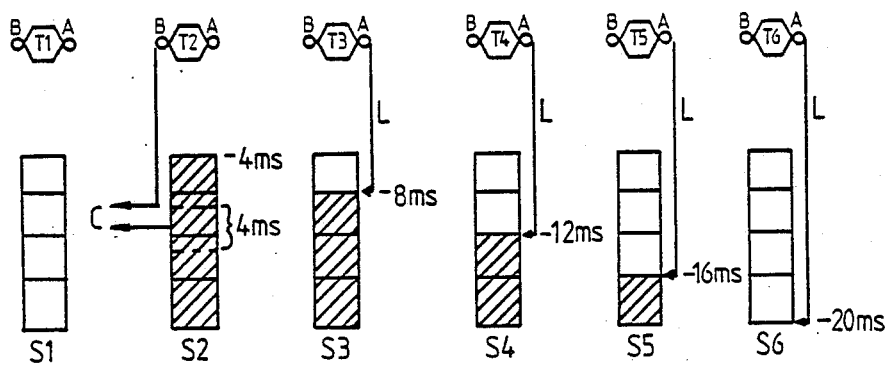

In a conventional false-twist crimping machine, having for example 24 yarn processing stations per bay and 9 such bays, it is convenient to provide monitoring apparatus as above described for each bay instead of for each processing station, thereby reducing considerably the cost of providing such apparatus for the machine. However if each yarn in a bay is monitored in succession the time lapse between successive monitorings of any one yarn would be such that many transient variations of crimp velocity could be missed. To overcome this problem an arrangement such as is shown in FIGS. 6 and 7 is used. Within the calculating means 29 there are provided signal stores 42, one for each yarn processing station 1 to 24 but only stores 51 to 56 corresponding to stations 1 to 6 being shown for clarity. Each store 42 is set to receive from its respective transducerT, 100 signals from amplifier output B in each of four delay band widths of 4 ms in an overall delay band of from 4 ms to 20 ms. If, as previously mentioned, the spacing of the measuring stations is 200 mm the overall delay band represents yarn throughput speeds of 300 m/min to 600 m/min. Other measuring station spacings and/or other delay band widths may be used if desired. When all of the data from processing station number 1 has been loaded into S1, ie the signal from transducer T1 output A with all of the incremental delays from 4 ms to 20 ms, the signal from transducer T1 output B and a 4 ms bandwidth of signals from the store S1 spanning the delay corresponding with the speed of yarn throughput, are fed to a correlator C of the calculator 29, as shown in FIG. 6. This reduces the correlation time to one quarter of that required if all of the information stored in S1 were to be fed to the correlator C. Whilst the correlation is being performed loading of data into the next four stores S2, S3, S4 and S5 takes place, each store's data being 4 ms delay spaced from the adjacent store's data. In consequence, when the correlation of the data from store S1 has been performed, all of the necessary data will have been loaded into store S2 and correlation of the signal from transducer T2 output B and a 4 ms bandwidth of signals from stores S2 may be fed to the correlator C as shown in FIG. 7. During the correlation of this data the loading of further data into stores S3, S4 and S5, and the loading of teh data into store S6 is carried out. This procedure is carried out for each processing station 1 to 24 in sequence. Since loading of four stores is performed simultaneously the time taken to complete the monitoring of all 24 processing stations is reduced to approximately one sixth of that which would be required if each store were to be loaded after the correlation of the data from the previous store had been effected. In consequence the risk of non-detection of transient variations in the crimp velocity of any one yarn is considerably reduced.

Alternative embodiments of apparatus in accordance with the invention will be readily apparent to persons skilled in the art. For example since there is a predetermined constant speed ratio between the intermediate feed roller device 21 and the third feed roller device 23 the peripheral speed of the third feed roller device 23 may be measured to determine V1 if desired. Also the second velocity measuring device 30 may be adapted to measure other parameters which are randomly distributed along, but travel with, the yarn 13, such as vibration, capacitance, reflectivity, temperature or the like. Also the second velocity measuring device 30 may be located between the intermediate feed device 21 and the second heater 22, or within the second heater 22, if preferred. If no second heater 22 is provided, or as an alternative to the use of a suction gun for threading purposes, the case 36 insulating body 35 and discs 34 may be provided with a threading slot so that the yarn 13 may be introduced laterally into the velocity measuring device 30.

Referring now to FIG. 8 there is shown a typical relationship between crimp velocity as measured in accordance with this invention and final bulk level on crimp retraction as measured by an off-line test as previously described. In this case a textured 78f34 polyester yarn has been evaluated and the crimp velocity and crimp retraction are shown to vary in a corresponding manner with primary heater temperature.

We claim:

1. A method of texturizing a yarn and simultaneously monitoring the quality of a crimped yarn produced during said yarn texturizing process, comprising the steps of:

forwarding a yarn to a crimping device in a texturizing zone and texturizing said yarn in said zone to insert a crimp therein;

measuring a first velocity of the crimped yarn whilst forwarding the crimped yarn through said zone from said crimping device under a first tension which is sufficient to draw out the crimp;

then forwarding the crimped yarn under a stabilizing second tension which is insufficient to draw out the crimp and measuring a second velocity of the yarn whilst so forwarding it;

and calculating a crimp velocity value from said yarn velocity measurements.

2. A method according to claim 1 comprising;

forwarding said crimped yarn through said texturizing zone, by means of a feed device, wherein said first velocity measurement is effected by measuring the peripheral speed of said yarn feed device.

3. A method according to claim 2 comprising feeding the yarn from said texturizing zone through a subsequent processiong region wherein said subsequent processing region has two spaced locations therein, and wherein said second velocity measurement is effected by detecting, at said two spaced locations, a parameter of said yarn which moves with said yarn, and measuring the elapsed time between such detections.

4. A method according to claim 3 wherein said second velocity measuring step comprises detecting at said two locations a static electrical charge carried by said yarn.

5. An apparatus for texturizing a yarn and simultaneously monitoring the quality of a crimped yarn produced during said texturizing comprising:

a texturizing zone and means disposed in said texturizing zone for crimping a yarn to insert a crimp therein;

first forwarding and tensioning means operable to forward the crimped yarn through said texturizing zone from said crimping means under a first tension sufficient to draw out the crimp therein;

first velocity measuring means operable to measure the velocity of the crimped yarn whilst it is forwarded under said first tension;

second forwarding and tensioning means operable to forward said crimped yarn under a second stabilising tension insufficient to draw out the crimp;

second velocity measuring means operable to measure the velocity of the crimped yarn whilst it is forwarded under said stabilizing second tenson; and calculating means operable to calculate a crimp velocity value from said yarn velocity measurements.

6. An apparatus according to claim 5 further comprising:

a subsequent processing apparatus, wherein said first forwarding and tensioning device comprises a feed device operable to feed said crimped yarn after it has passed through said crimping means, and wherein said first velocity measuring means is operable to measure the peripheral speed of said feed device.

7. Apparatus according to claim 5 comprising two spaced locations, wherein said second velocity measuring means comprises detecting means operable to detect at said two spaced locations a parameter of the yarn which moves with the yarn, and time measuring means operable to measure the elapsed time between such detections.

8. Apparatus according to claim 7 wherein said detecting means comprises static electrical charge measuring means.

9. An apparatus, according to claim 7 wherein said second velocity measuring means comprises:

a housing in which two spaced locations are located and which defines a path of travel of the yarn therethrough; and said detecting means comprises at each location a sensor adapted to detect the presence of a static electric charge on said yarn and to produce an electrical signal proportional to the value of said static electric charge.

10. Apparatus according to claim 9 wherein each sensor comprises a disc of an electrically conductive material having an aperture therein through which a yarn may pass.

11. Apparatus according to claim 10 comprising a body of an electrically insulating material, wherein said discs are separated by said body.

12. Apparatus according to claim 11 wherein said housing comprises a case of an elecrically conductive material and which encloses said discs and said insulating body.

13. Apparatus according to claim 10 comprising an amplifier and having an input respective to each disc, wherein each disc is electrically connected to said respective input of said amplifier and then to said calculating means.

14. Apparatus according to claim 13 wherein said amplifier is a high impedance, non-inverting, negative feedback operational amplifier having a leakage resistor disposed between each of said inputs and a zero volt (earth) lead.

15. Apparatus according to claim 14 wherein each of said resistors has a value of substantially 180 K$\Omega$.

16. An apparatus according to claim 13, wherein said calculating means comprises:

delay means operable to apply a delay to said signal from said sensor at said first location; and correlating means operable to cross-correlate said delayed signal with said signal from said sensor at said second location.

17. Apparatus according to claim 9 wherein said locations are spaced substantially 200 mm apart.

18. A false twist crimping machine having a plurality of yarn processing stations, and for each of said stations an apparatus according to claim 5, wherein each second velocity measuring means comprises:

a housing having first and second spaced locations therein and detecting means at each of said spaced locations operable to detect a parameter of the yarn which moves with the yarn and to produce an electrical signal proportional to the value of said parameter, and wherein said calculating means comprises signal store means for each of a set of said yarn processing stations each to receive said signal from a respective measuring means.

19. A false twist crimping machine according to claim 18 wherein said calculating means comprises correlating means operable to cross-correlate said signals from said detecting means at said spaced locations of said second velocity measuring means at a first yarn processing station of said yarn set, simultaneously with said calculating means receiving into a respective signal store means said signals from at least one other measuring means at an adjacent yarn processing station of said set, and to repeat said operation in sequence for each of said yarn processing stations of said set.

20. A false twist crimping machine according to claim 19, wherein four measuring means at adjacent yarn processing stations are adapted to produce signals which are received simultaneously into the respective signal store means of said calculating means.

* * * * *